United States Patent
Rudnic et al.

(10) Patent No.: US 6,929,804 B2
(45) Date of Patent: *Aug. 16, 2005

(54) ANTI-FUNGAL COMPOSITION

(75) Inventors: Edward M. Rudnic, N. Potomac, MD (US); James D. Isbister, Potomac, MD (US); Donald J. Treacy, Jr., Annapolis, MD (US); Sandra E. Wassink, Frederick, MD (US)

(73) Assignee: Advancis Pharmaceutical Corp., Germantown, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/320,113

(22) Filed: Dec. 16, 2002

(65) Prior Publication Data

US 2003/0203023 A1 Oct. 30, 2003

Related U.S. Application Data

(63) Continuation of application No. 09/791,284, filed on Feb. 23, 2001, now abandoned.

(51) Int. Cl.$^7$ ............................ A61K 9/00; A61K 9/20; A61K 9/22; A61K 9/54; A61K 9/14
(52) U.S. Cl. ...................... 424/468; 424/400; 424/457; 424/464; 424/471; 424/472; 424/484; 424/489; 514/964
(58) Field of Search ................................ 424/400, 422, 424/451, 457, 458, 464, 468, 471, 472, 484, 490; 514/960, 964

(56) References Cited

U.S. PATENT DOCUMENTS

| | | | |
|---|---|---|---|
| 4,435,173 A | 3/1984 | Siposs et al. | 609/155 |
| 4,616,008 A | 10/1986 | Hirai et al. | 514/200 |
| 4,794,001 A | 12/1988 | Mehta et al. | 424/458 |
| 4,831,025 A | 5/1989 | Godtfredsen et al. | 514/195 |
| 4,904,476 A | 2/1990 | Mehta et al. | 424/456 |
| 4,915,953 A | 4/1990 | Jordan et al. | 424/473 |
| 4,971,805 A | 11/1990 | Kitanishi et al. | 424/494 |
| 5,011,692 A | 4/1991 | Fujioka et al. | 424/426 |
| 5,110,597 A | 5/1992 | Wong et al. | 424/438 |
| 5,213,808 A | 5/1993 | Bar-Shalom et al. | 424/473 |
| 5,229,131 A | 7/1993 | Amidon et al. | 424/451 |
| 5,395,626 A | 3/1995 | Kotwal et al. | 424/472 |
| 5,401,512 A | 3/1995 | Rhodes et al. | 424/458 |
| 5,413,777 A | 5/1995 | Sheth et al. | 424/490 |
| 5,414,014 A | 5/1995 | Schneider et al. | 514/535 |
| 5,445,829 A | 8/1995 | Paradissis et al. | 424/480 |
| 5,462,747 A | 10/1995 | Radebaugh et al. | 424/465 |
| 5,472,708 A | 12/1995 | Chen | 424/451 |
| 5,508,040 A | 4/1996 | Chen | 424/451 |
| 5,538,954 A | 7/1996 | Koch et al. | 514/53 |
| 5,567,441 A | 10/1996 | Chen | 424/494 |
| 5,672,359 A | 9/1997 | Digenis et al. | 424/463 |
| 5,719,132 A | 2/1998 | Lin et al. | 514/50 |
| 5,827,531 A | 10/1998 | Morrison et al. | 424/450 |
| 5,840,329 A | 11/1998 | Bai | 424/458 |
| 5,877,243 A | 3/1999 | Sarangapani | 524/139 |
| 5,883,079 A | 3/1999 | Zopf et al. | 514/25 |
| 5,910,322 A | 6/1999 | Rivett et al. | 424/484 |
| 6,027,748 A | 2/2000 | Conte et al. | 424/458 |
| 6,068,859 A | 5/2000 | Curatolo et al. | 424/490 |
| 6,120,803 A | 9/2000 | Wong et al. | 424/473 |
| 6,132,771 A | 10/2000 | Depui et al. | 424/468 |
| 6,157,491 A | * 12/2000 | Watanabe et al. | 359/619 |
| 6,159,491 A | * 12/2000 | Durrani | 424/430 |
| 6,294,199 B1 | 9/2001 | Conley et al. | 424/468 |
| 6,358,525 B1 | 3/2002 | Guo et al. | 424/464 |
| 6,541,014 B2 | 4/2003 | Rudnic et al. | 424/400 |
| 6,544,555 B2 | 4/2003 | Rudnic et al. | 424/468 |
| 6,565,882 B2 | 5/2003 | Rudnic | 424/472 |
| 2001/0046984 A1 | 11/2001 | Rudnic et al. | 514/210.09 |
| 2001/0048944 A1 | 12/2001 | Rudnic et al. | 424/468 |
| 2002/0004070 A1 | 1/2002 | Rudnic et al. | 424/468 |
| 2002/0004499 A1 | 1/2002 | Rudnic et al. | 514/192 |
| 2002/0068078 A1 | 6/2002 | Rudnic et al. | 424/408 |
| 2002/0068085 A1 | 6/2002 | Rudnic et al. | 424/468 |
| 2002/0119168 A1 | 8/2002 | Rudnic et al. | 424/400 |
| 2002/0136764 A1 | 9/2002 | Rudnic et al. | 424/457 |
| 2002/0136765 A1 | 9/2002 | Rudnic et al. | 424/457 |
| 2002/0136766 A1 | 9/2002 | Rudnic et al. | 424/457 |
| 2002/0150619 A1 | 10/2002 | Rudnic et al. | 424/468 |
| 2002/0197314 A1 | 12/2002 | Rudnic et al. | 424/468 |
| 2003/0012814 A1 | 1/2003 | Rudnic et al. | 424/468 |
| 2003/0066410 A1 | 4/2003 | Rudnic et al. | 424/468 |
| 2003/0077323 A1 | 4/2003 | Rudnic et al. | 424/468 |
| 2003/0086969 A1 | 5/2003 | Rudnic et al. | 424/486 |
| 2003/0096006 A1 | 5/2003 | Rudnic et al. | 424/468 |
| 2003/0096007 A1 | 5/2003 | Rudnic et al. | 424/468 |
| 2003/0096008 A1 | 5/2003 | Rudnic et al. | 424/468 |
| 2003/0099706 A1 | 5/2003 | Rudnic et al. | 424/468 |
| 2003/0099707 A1 | 5/2003 | Rudnic et al. | 424/468 |
| 2003/0104054 A1 | 6/2003 | Rudnic et al. | 424/468 |
| 2003/0104055 A1 | 6/2003 | Rudnic et al. | 424/468 |
| 2003/0104056 A1 | 6/2003 | Rudnic et al. | 424/468 |
| 2003/0104058 A1 | 6/2003 | Rudnic et al. | 424/468 |

FOREIGN PATENT DOCUMENTS

| | | |
|---|---|---|
| EP | 0652008 A1 | 5/1995 |
| WO | WO 94/27557 | 12/1994 |
| WO | WO 95/20946 | 8/1995 |
| WO | WO 96/04908 | 2/1996 |
| WO | WO 98/22091 | 5/1998 |

OTHER PUBLICATIONS

Erah et al.; The Stability of amoxycillin, clarithromycin and metronidazole in gastric juice: relevance to the treatment of Helibacter pylori infection.; Jan. 1997; Journal of Antimicrob. Chemother. 39(1):5–12. PMID: 9044021.

Yousef et al.: Combined action of amoxycillin and dicloxicillin against *Staphylococcus aureus* in vitro; Sep. 1985; Pharmazie; 40(9):650–1 PMID: 3877939.

Gnarpe et al.; Pencillin combinations against multi-resistant urinary pathogens as an alternative to gentamycin treatment; 1976; Microbios.; 16(65–66):201–6 PMID: 18651.

Polak, Pharmacokinetics of amphotericin B and flucytosine, Postgraduate Medical Journal, (647) pp. 667–670, Sep. 1979).*

* cited by examiner

*Primary Examiner*—Michael Hartley
*Assistant Examiner*—Sharmila S. Gollamudi
(74) *Attorney, Agent, or Firm*—Elliot M. Olstein; Raymond E. Stauffer

(57) ABSTRACT

An anti-fungal product for delivering at least two different anti-fungals that is comprised of three dosage forms with different release profiles with each anti-fungal being present in at least one of the dosage forms.

39 Claims, No Drawings

ANTI-FUNGAL COMPOSITION

This application is a continuation of U.S. application Ser. No. 09/791,284, filed on Feb. 23, 2001 now abandoned.

This invention relates to anti-fungal compositions and the use thereof. More particularly, this invention relates to a composition for the delivery of two or more anti-fungals, and the use thereof.

In many cases, it is desirable to employ two different anti-fungals in the treatment of a fungus infection, in that such anti-fungals may have complementary mechanisms of action that facilitate treatment of the fungus infection.

The present invention is directed to a new and improved composition that delivers two or more anti-fungals, and the use thereof.

In accordance with an aspect of the present invention, there is provided an anti-fungal product for delivering at least two different anti-fungals that is comprised of at least three dosage forms each comprised of at least one anti-fungal agent and a pharmaceutically acceptable carrier, with one of the dosage forms including at least one of the at least two anti-fungals and at least one dosage form including at least a second anti-fungal of the at least two anti-fungals.

Thus, for example, each of the dosage forms may include two or more anti-fungals, or one or two of the dosage forms may include only one of the two or more anti-fungals and each of the remaining dosage forms may include only one or more of the different anti-fungals or two or more of the anti-fungals. Thus, in accordance with this aspect of the invention, there is an anti-fungal product for delivering at least two different anti-fungals wherein the product includes at least three dosage forms wherein each of the at least two anti-fungals is present in at least one of the three dosage forms.

In a preferred embodiment each of the dosage forms has a different release profile, with one of the dosage forms being an immediate release dosage form.

In another aspect, the present invention is directed to treating a fungus infection by administering to a host in need thereof an anti-fungal product as hereinabove and hereinafter described.

Thus, in accordance with an aspect of the present invention, there is provided a single or unitary anti-fungal product that has contained therein at least three anti-fungal dosage forms, each of which has a different release profile, whereby the anti-fungal contained in each of the at least three dosage forms is released at different times, and wherein at least one of the dosage forms includes at least a first anti-fungal and at least one of the dosage forms includes at least a second anti-fungal different from the first anti-fungal.

In accordance with a further aspect of the invention, the anti-fungal product may be comprised of at least four different dosage forms, each of which starts to release the anti-fungal contained therein at different times after administration of the anti-fungal product.

The anti-fungal product generally does not include more than five dosage forms with different release times.

In accordance with a preferred embodiment, the anti-fungal product has an overall release profile such that when administered the maximum serum concentration of the total anti-fungal released from the product is reached in less than twelve hours, preferably in less than eleven hours. In an embodiment, the maximum serum concentration of the total anti-fungal released from the anti-fungal product is achieved no earlier than four hours after administration.

In accordance with one preferred embodiment of the invention, one of the at least three dosage forms is an immediate release dosage form whereby initiation of release of anti-fungal therefrom is not substantially delayed after administration of the anti-fungal product. The second and third of the at least three dosage forms is a delayed dosage form (which may be a pH sensitive or a non-pH sensitive delayed dosage form, depending on the type of anti-fungal product), whereby anti-fungal released therefrom is delayed until after initiation of release of anti-fungal from the immediate release dosage form. More particularly, anti-fungal release from the second of the at least two dosage forms achieves a $C_{max}$ (maximum serum concentration in the serum) at a time after anti-fungal released from the first of the at least three dosage forms achieves a $C_{max}$ in the serum, and anti-fungal released from the third dosage form achieves a $C_{max}$ in the serum after the $C_{max}$ of anti-fungal released from the second dosage form.

In one embodiment, the second of the at least two dosage forms initiates release of anti-fungal contained therein at least one hour after the first dosage form, with the initiation of the release therefrom generally occurring no more than six hours after initiation of release of anti-fungal from the first dosage form of the at least three dosage forms.

In general, the immediate release dosage form produces a $C_{max}$ for anti-fungal released therefrom within from about 0.5 to about 2 hours, with the second dosage form of the at least three dosage forms producing a $C_{max}$ for anti-fungal released therefrom in no more than about four hours. In general, the $C_{max}$ for such second dosage form is achieved no earlier than two hours after administration of the anti-fungal product; however, it is possible within the scope of the invention to achieve $C_{max}$ in a shorter period of time.

As hereinabove indicated, the anti-fungal product may contain at least three or at least four or more different dosage forms. For example, the anti-fungal released from the third dosage form reaches a $C_{max}$ at a time later than the $C_{max}$ is achieved for anti-fungal released from each of the first and second dosage forms. In a preferred embodiment, release of anti-fungal from the third dosage form is started after initiation of release of anti-fungal from both the first dosage form and the second dosage form. In one embodiment, $C_{max}$ for anti-fungal release from the third dosage form is achieved within eight hours.

In another embodiment, the anti-fungal product contains at least four dosage forms, with each of the at least four dosage forms having different release profiles, whereby anti-fungal released from each of the at least four different dosage forms achieves a $C_{max}$ at a different time.

As hereinabove indicated, in a preferred embodiment, irrespective of whether the anti-fungal contains at least three or at least four different dosage forms each with a different release profile, $C_{max}$ for all the anti-fungal released from the anti-fungal product is achieved in less than twelve hours, and more generally is achieved in less than eleven hours.

In a preferred embodiment, the anti-fungal product is a once a day product, whereby after administration of the anti-fungal product, no further product is administered during the day; i.e., the preferred regimen is that the product is administered only once over a twenty-four hour period. Thus, in accordance with the present invention, there is a single administration of an anti-fungal product with the anti-fungal being released in a manner such that overall anti-fungal release is effected with different release profiles in a manner such that the overall $C_{max}$ for the anti-fungal product is reached in less than twelve hours. The term single administration means that the total anti-fungal administered over a twenty-four hour period is administered at the same time, which can be a single tablet or capsule or two or more thereof, provided that they are administered at essentially the same time.

Thus in accordance with an aspect of the invention, there is provided a single dosage anti-fungal product comprised of at least three anti-fungal dosage forms each having a different release profile with each of the dosage forms including at least one of a first or second anti-fungal and at least one of the three dosage forms including at least the first anti-fungal and at least one of the dosage forms including at least the second anti-fungal. Each of the dosage forms of anti-fungal in a pharmaceutically acceptable carrier may have one or more anti-fungals.

It is to be understood that when it is disclosed herein that a dosage form initiates release after another dosage form, such terminology means that the dosage form is designed and is intended to produce such later initiated release. It is known in the art, however, notwithstanding such design and intent, some "leakage" of anti-fungal may occur. Such "leakage" is not "release" as used herein.

If at least four dosage forms are used, the fourth of the at least four dosage form may be a sustained release dosage form or a delayed release dosage form. If the fourth dosage form is a sustained release dosage form, even though $C_{max}$ of the fourth dosage form of the at least four dosage forms is reached after the $C_{max}$ of each of the other dosage forms is reached, anti-fungal release from such fourth dosage form may be initiated prior to or after release from the second or third dosage form.

In accordance with an aspect of the present invention, there is provided an anti-fungal composition that is a mixture of anti-fungal compositions or dosage forms wherein said composition contains a first composition or dosage form comprising a first anti-fungal and a pharmaceutically acceptable carrier; a second composition or dosage form comprising the first anti-fungal and a pharmaceutically acceptable carrier; a third composition or dosage form comprising a second anti-fungal different from the first anti-fungal and a pharmaceutically acceptable carrier; and a fourth composition or dosage form comprising the second anti-fungal and a pharmaceutically acceptable carrier; wherein the second and third compositions each have a release profile that provides a maximum serum concentration of the first anti-fungal released from the second composition and a maximum serum concentration for the second anti-fungal released from the third composition at a time after the first anti-fungal released from the first composition reaches a maximum serum concentration, and wherein the fourth composition has a release profile that provides for a maximum serum concentration of the second anti-fungal released from the fourth composition at a time after the anti-fungals released from the second and third compositions reach a maximum serum concentration.

In one embodiment, the release profiles of the second and third composition are such that the maximum serum concentration of the first anti-fungal released from the second composition, and the maximum serum concentration of the second anti-fungal released from the third composition are reached at approximately the same time, or where the first anti-fungal reaches a maximum serum concentration before or after the second anti-fungal reaches a maximum serum concentration.

In effect, in accordance with a preferred embodiment of the present invention, there is provided a first pulse in which a first anti-fungal reaches a maximum serum concentration, a second pulse wherein a further dosage of the first anti-fungal, and an initial dosage of the second anti-fungal reach a maximum serum concentration at a time after the first pulse of the first anti-fungal reaches a maximum serum concentration, and a third pulse wherein an additional dosage of the second anti-fungal reaches a maximum serum concentration at a time after the maximum serum concentration is reached for each of the first and second anti-fungal dosages provided in the second pulse.

In a preferred embodiment of the present invention, the first dosage of the first anti-fungal achieves a maximum serum concentration within four hours after administration of the anti-fungal composition; the second dosage of the first anti-fungal and the first dosage of the second anti-fungal each reach a maximum serum concentration within four to eight hours after administration of the anti-fungal composition; and the second dosage of the second anti-fungal reaches a maximum serum concentration within twelve hours after administration of the anti-fungal composition.

Thus, in accordance with an aspect of the present invention, there is provided an anti-fungal composition that includes four different dosage forms, with the first dosage form providing an initial dosage of a first anti-fungal, the second dosage form providing a further dosage of the first anti-fungal; the third dosage form providing an initial dosage of a second anti-fungal; and the fourth dosage form providing an additional dosage of the second anti-fungal, wherein the anti-fungals released from the second and third dosage forms reach a maximum serum concentration at a time after the anti-fungal released from the first dosage form reaches a maximum serum concentration, and the anti-fungal released from the fourth dosage form reaching a maximum serum concentration at a time after the times at which the anti-fungals released from each of the first, second, and third dosage forms reach a maximum serum concentration.

In one embodiment of the invention, the first dosage form provides for immediate release, the second and third dosage forms provide for a delayed release (pH or non pH dependent, with the second dosage form preferably being a pH dependent release), and the fourth dosage form provides for pH dependent or non pH dependent release preferably non pH dependent release.

In formulating the anti-fungal composition of the present invention, which contains four different dosage forms, as hereinabove described, the first dosage form generally contains from about 30 percent to about 80 percent of the first anti-fungal; the second dosage form contains from about 30 percent to about 80 percent of the first anti-fungal; the third dosage form contains from about 30 percent to about 80 percent of the second anti-fungal, and the fourth anti-fungal dosage form contains from about 30 percent to about 80 percent of the second anti-fungal. In formulating a composition comprised of such four dosage forms or units, each unit or dosage form is present in an amount of at least 20 percent by weight, with each dosage form or unit being present in the overall composition in an amount that generally does not exceed 60 percent by weight.

Each of the first and second dosage forms include from 20% to 80% of the total dosage of the first anti-fungal to be provided by the composition, and each of the first and second dosage forms may include the same or different dosages of the first anti-fungal.

Each of the third and fourth dosage forms include from 20% to 80% of the total dosage of the second anti-fungal to be delivered by the composition, and each of the third and fourth units may have the same or different dosages of the anti-fungal.

In formulating an anti-fungal product in accordance with the invention, in one embodiment, the immediate release dosage form of the product generally provides from about 20% to about 50% of the total dosage of anti-fungal to be delivered by the product, with such immediate release dosage form generally providing at least 25% of the total dosage of the anti-fungal to be delivered by the product. In many cases, the immediate release dosage form provides from about 20% to about 30% of the total dosage of anti-fingal to be delivered by the product; however, in some cases it may be desirable to have the immediate release dosage form provide for about 45% to about 50% of the total dosage of anti-fungal to be delivered by the product.

The remaining dosage forms deliver the remainder of the anti-fungal. If more than one delayed release dosage form is used, in one embodiment, each of the delayed release dosage forms may provide about equal amounts of anti-fungal; however, they may also be formulated so as to provide different amounts.

In one embodiment, where the composition contains one immediate release component and two delayed release components, the immediate release component provides from 20% to 35% (preferably 20% to 30%), by weight, of the total anti-fungal; where there is three delayed release components, the immediate release component provides from 15% to 30%, by weight, of the total anti-fungal; and where there are four delayed release components, the immediate release component provides from 10% to 25%, by weight, of the total anti-fungal.

With respect to the delayed release components, where there are two delayed release components, the first delayed release component (the one released earlier in time) provides from 30% to 60%, by weight, of the total anti-fungal provided by the two delayed release components with the second delayed release component providing the remainder of the anti-fungal.

Where there are three delayed release components, the earliest released component provides 20% to 35% by weight of the total anti-fungal provided by the three delayed release components, the next in time delayed release component provides from 20% to 40%, by weight, of the anti-fungal provided by the three delayed release components and the last in time providing the remainder of the anti-fungal provided by the three delayed release components.

When there are four delayed release components, the earliest delayed release component provides from 15% to 30%, by weight, the next in time delayed release component provides from 15% to 30%, the next in time delayed release component provides from 20% to 35%, by weight, and the last in time delayed release component provides from 20% to 35%, by weight, in each case of the total anti-fungal provided by the four delayed release components.

The overall composition includes each of the anti-fungals in a therapeutically effective amount. The specific amount(s) is dependant on the anti-fungal used, the disease or infection to be treated, and the number of times of day that the composition is to be administered.

The anti-fungal composition of the present invention may be administered for example, by any one of the following routes of administration: sublingual, transmucosal, transdermal, parenteral, oral, preferably by oral administration.

The anti-fungal product of the present invention, as hereinabove described, may be formulated for administration by a variety of routes of administration. For example, the anti-fungal product may be formulated in a way that is suitable for topical administration; administration in the eye or the ear; rectal or vaginal administration; as nose drops; by inhalation; as an injectable; or for oral administration. In a preferred embodiment, the anti-fungal product is formulated in a manner such that it is suitable for oral administration.

For example, in formulating the anti-fungal product for topical administration, such as by application to the skin, the at least two different dosage forms, each of which contains an anti-fungal, may be formulated for topical administration by including such dosage forms in an oil-in-water emulsion, or a water-in-oil emulsion. In such a formulation, the immediate release dosage form is in the continuous phase, and the delayed release dosage form is in a discontinuous phase. The formulation may also be produced in a manner for delivery of three dosage forms as hereinabove described. For example, there may be provided an oil-in-water-in-oil emulsion, with oil being a continuous phase that contains the immediate release component, water dispersed in the oil containing a first delayed release dosage form, and oil dispersed in the water containing a third delayed release dosage form.

It is also within the scope of the invention to provide an anti-fungal product in the form of a patch, which includes anti-fungal dosage forms having different release profiles, as hereinabove described.

In addition, the anti-fungal product may be formulated for use in the eye or ear or nose, for example, as a liquid emulsion. For example, the dosage form may be coated with a hydrophobic polymer whereby a dosage form is in the oil phase of the emulsion, and a dosage form may be coated with hydrophilic polymer, whereby a dosage form is in the water phase of the emulsion.

Furthermore, the anti-fungal product with at least three different dosage forms with different release profiles may be formulated for rectal or vaginal administration, as known in the art. This may take the form of a cream or emulsion, or other dissolvable dosage form similar to those used for topical administration.

As a further embodiment, the anti-fungal product may be formulated for use in inhalation therapy by coating the particles and micronizing the particles for inhalation.

In a preferred embodiment, the anti-fungal product is formulated in a manner suitable for oral administration. Thus, for example, for oral administration, each of the dosage forms may be used as a pellet or a particle, with a pellet or particle then being formed into a unitary pharmaceutical product, for example, in a capsule, or embedded in a tablet, or suspended in a liquid for oral administration.

Alternatively, in formulating an oral delivery system, each of the dosage forms of the product may be formulated as a tablet, with each of the tablets being put into a capsule to produce a unitary anti-fungal product. Thus, for example, anti-fungal products may include a first dosage form in the form of a tablet that is an immediate release tablet, and may also include two or more additional tablets, each of which provides for a delayed release of the anti-fungal, as hereinabove described, whereby the $C_{max}$ of the anti-fungal released from each of the tablets is reached at different times, with the $C_{max}$ of the total anti-fungal released from the anti-fungal product being achieved in less than twelve hours.

The formulation of an anti-fungal product including at least three dosage forms with different release profiles for different routes of administration is deemed to be within the skill of the art from the teachings herein. As known in the art, with respect to delayed release, the time of release can be controlled by the concentration of anti-fungals in the coating and/or the thickness of the coating.

The Immediate Release Component

The immediate release portion of this system can be a mixture of ingredients that breaks down quickly after administration to release the anti-fungal. This can take the form of either a discrete pellet or granule that is mixed in with, or compressed with, the other three components.

The materials to be added to the anti-fungals for the immediate release component can be, but are not limited to, microcrystalline cellulose, corn starch, pregelatinized starch, potato starch, rice starch, sodium carboxymethyl starch, hydroxypropylcellulose, ydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000-10000) and high molecular weight PEGs (Polyox) with molecular weights above 20,000 daltons.

It may be useful to have these materials present in the range of 1.0 to 60% (W/W).

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above.

These materials may be present in the rate of 0.05–15% (W/W).

The Delayed Release Component

The components in this composition are the same immediate release unit, but with additional polymers integrated into the composition, or as coatings over the pellet or granule.

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

Typically these materials can be present in the range of 0.5–25% (W/W) of this component.

The Enteric Release Component

The components in this composition are the same as the immediate release component, but with additional polymers integrated into the composition, or as coatings over the pellet or granule.

The kind of materials useful for this purpose can be, but are not limited to, cellulose acetate pthalate, Eudragit L, and other pthalate salts of cellulose derivatives.

These materials can be present in concentrations from 4–20% (W/W).

The following are representative examples of some anti-fungals that can be employed in the composition of the invention: amphotericin B, flucytosine, fluconazole, griseofulvin, miconazole nitrate, terbinafine hydrochloride, ketoconazole, itraconazole, undecylenic acid and chloroxylenol, ciclopirox, clotrimazole, butenafine hydrochloride, nystatin, naftifine hydrochloride, oxiconazole nitrate, selenium sulfide, econazole nitrate, terconazole, butoconazole nitrate, carbol-fuchsin, clioquinol, methylrosaniline chloride, sodium thiosulfate, sulconazole nitrate, terbinafine hydrochloride, tioconazole, tolnaftate, undecylenic acid and undecylenate salts (calcium undecylenate, copper undecylenate, zinc undecylenate)

The invention will be further described with respect to the following examples; however, the scope of the invention is not limited thereby. All percentages in this specification, unless otherwise specified, are by weight.

Immediate Release Component

Formulate the composition by mixing the ingredients in a suitable pharmaceutical mixer or granulator such as a planetary mixer, high-shear granulator, fluid bed granulator, or extruder, in the presence of water or other solvent, or in a dry blend. If water or other solvent was used, dry the blend in a suitable pharmaceutical drier, such as a vacuum oven or forced-air oven. The product may be sieved or granulated, and compressed using a suitable tablet press, such as a rotary tablet press.

EXAMPLE 1

| | |
|---|---|
| Fluconazole | 65% (W/W) |
| Microcrystalline cellulose | 20 |
| Povidone | 10 |
| Croscarmellose sodium | 5 |

EXAMPLE 2

| | |
|---|---|
| Fluconazole | 55% (W/W) |
| Microcrystalline cellulose | 25 |
| Povidone | 10 |
| Croscarmellose sodium | 10 |

EXAMPLE 3

| | |
|---|---|
| Fluconazole | 65% (W/W) |
| Microcrystalline cellulose | 20 |
| Hydroxypropylcellulose | 10 |
| Croscarmellose sodium | 5 |

EXAMPLE 4

| | |
|---|---|
| Fluconazole | 75% (W/W) |
| Polyethylene glycol 4000 | 10 |
| Polyethylene glycol 2000 | 10 |
| Hydroxypropylcellulose | 5 |

EXAMPLE 5

| | |
|---|---|
| Fluconazole | 75% (W/W) |
| Polyethylene glycol 8000 | 20 |
| Polyvinylpyrrolidone | 5 |

EXAMPLE 6

| | |
|---|---|
| Ketoconazole | 65% (W/W) |
| Microcrystalline cellulose | 20 |
| Hydroxypropylcellulose | 10 |
| Croscarmellose sodium | 5 |

EXAMPLE 7

| Ketoconazole | 75% (W/W) |
|---|---|
| Microcrystalline cellulose | 15 |
| Hydroxypropylcellulose | 5 |
| Croscarmellose sodium | 5 |

EXAMPLE 8

| Ketoconazole | 75% (W/W) |
|---|---|
| Polyethylene glycol 4000 | 10 |
| Polyethylene glycol 2000 | 10 |
| Hydroxypropylcellulose | 5 |

EXAMPLE 9

| Ketoconazole | 75% (W/W) |
|---|---|
| Polyethylene glycol 8000 | 20 |
| Polyvinylpyrrolidone | 5 |

EXAMPLE 10

| Griseofulvin | 65% (W/W) |
|---|---|
| Microcrystalline cellulose | 20 |
| Hydroxypropylcellulose | 10 |
| Croscarmellose sodium | 5 |

EXAMPLE 11

| Griseofulvin | 75% (W/W) |
|---|---|
| Microcrystalline cellulose | 15 |
| Hydroxypropylcellulose | 5 |
| Croscarmellose sodium | 5 |

EXAMPLE 12

| Griseofulvin | 75% (W/W) |
|---|---|
| Polyethylene glycol 4000 | 10 |
| Polytheylene glycol 2000 | 10 |
| Hydroxypropylcellulose | 5 |

EXAMPLE 13

| Cirpofloxacin | 75% (W/W) |
|---|---|
| Polyethylene glycol 8000 | 20 |
| Polyvinylpyrrolidone | 5 |

EXAMPLE 14

| Terbinafine HCl | 75% (W/W) |
|---|---|
| Polyethylene glycol 4000 | 10 |
| Polyethylene glycol 2000 | 10 |
| Hydroxypropylcellulose | 5 |

EXAMPLE 15

| Terbinafine HCl | 75% (W/W) |
|---|---|
| Polyethylene Glycol 4000 | 20 |
| Polyvinylpyrrolidone | 5 |

Non pH Sensitive Delayed Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven. Allow the product to cool, the product may be sieved or granulated, and compressed using a suitable tablet press, such as a rotary tablet press.

|  | Ingredient | Conc. (% W/W) |
|---|---|---|
| Example 16: | Fluconazole | 65% (W/W) |
|  | Microcrystalline cellulose | 20 |
|  | Polyox | 10 |
|  | Croscarmellose sodium | 5 |
| Example 17: | Fluconazole | 55% (W/W) |
|  | Microcrystalline cellulose | 25 |
|  | Polyox | 10 |
|  | Glyceryl monooleate | 10 |
| Example 18: | Fluconazole | 65% (W/W) |
|  | Polyox | 20 |
|  | Hydroxypropylcellulose | 10 |
|  | Croscarmellose sodium | 5 |
| Example 19: | Ketoconazole | 70% (W/W) |
|  | Polyox | 20 |
|  | Hydroxypropylcellulose | 5 |
|  | Croscarmellose sodium | 5 |

Enteric Release Component

Formulate the ingredients by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven. Allow the product to cool, the product may be sieved or granulated, and compressed using a suitable tablet press, such as a rotary tablet press.

|  | Ingredient | Conc. (% W/W) |
|---|---|---|
| Example 20: | Fluconazole | 65% (W/W) |
|  | Microcrystalline cellulose | 20 |
|  | Cellulose Acetate Pthalate | 15 |
| Example 21: | Fluconazole | 55% (W/W) |
|  | Microcrystalline cellulose | 25 |
|  | Cellulose Acetate Pthalate | 10 |
|  | Hydroxypropylmethylcellulose | 10 |

-continued

| | Ingredient | Conc. (% W/W) |
|---|---|---|
| Example 22: | Fluconazole | 65% (W/W) |
| | Polyox | 20 |
| | Hydroxypropylcellulose pthalate | 10 |
| | Eudragit L30D | 5 |
| Example 23: | Fluconazole | 40% (W/W) |
| | Microcrystalline Cellulose | 40 |
| | Cellulose Acetate Pthalate | 10 |
| Example 24: | Ketoconazole | 70% (W/W) |
| | Hydroxypropylcellulose pthalate | 15 |
| | Croscarmellose sodium | 10 |
| Example 25: | Ketoconazole | 75% (W/W) |
| | Polyethylene glycol 2000 | 10 |
| | Eudragit L 30D | 15 |
| Example 26: | Ketoconazole | 40% (W/W) |
| | Lactose | 50 |
| | Eudgragit L 30D | 10 |
| Example 27: | Griseofulvin | 65% (W/W) |
| | Microcrystalline Cellulose | 20 |
| | Eudragit L 30D | 10 |
| Example 28: | Griseofulvin | 75% (W/W) |
| | Microcrystalline Cellulose | 15 |
| | Hydroxypropylcellulose pthalate | 10 |
| Example 29: | Griseofulvin | 80% (W/W) |
| | Lactose | 10 |
| | Eudragit L 30D | 10 |
| Example 30: | Griseofulvin | 70% (W/W) |
| | Polyethylene glycol 4000 | 20 |
| | Cellulose acetate pthalate | 10 |
| Example 31: | Terbinafine HCl | 60% (W/W) |
| | Polyethylene glycol 2000 | 10 |
| | Lactose | 20 |
| | Eudragit L 30D | 10 |
| Example 32: | Terbinafine HCl | 70% (W/W) |
| | Microcrystalline cellulose | 20 |
| | Cellulose acetate pthalate | 10 |

Sustained Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven. Allow the product to cool, the product may be sieved or granulated, and compressed using a suitable tablet press, such as a rotary tablet press.

| | Ingredient | Conc. (% W/W) |
|---|---|---|
| Example 33: | Fluconazole | 65% (W/W) |
| | Ethylcellulose | 20 |
| | Polyox | 10 |
| | Hydroxypropylmethylcellulose | 5 |
| Example 34: | Fluconazole | 55% (W/W) |
| | Lactose | 25 |
| | Polyox | 10 |
| | Glyceryl monooleate | 10 |
| Example 35: | Fluconazole | 70% (W/W) |
| | Polyox | 20 |
| | Hydroxypropylcellulose | 10 |
| Example 36: | Ketoconazole | 75% (W/W) |
| | Lactose | 15 |
| | Hydroxypropylcellulose | 5 |
| | Ethylcellulose | 5 |
| Example 37: | Ketoconazole | 75% (W/W) |
| | Polyethylene glycol 4000 | 10 |
| | Lactose | 10 |
| | Eudragit RL 30D | 5 |
| Example 38: | Ketoconazole | 80% (W/W) |
| | Polyethylene glycol 8000 | 10 |
| | Hydroxypropylmethylcellulose | 5 |
| | Eudragit RS 30D | 5 |

-continued

| | Ingredient | Conc. (% W/W) |
|---|---|---|
| Example 39: | Griseofulvin | 75% (W/W) |
| | Hydroxyethylcellulose | 10 |
| | Polyethylene glycol 4000 | 10 |
| | Hydroxypropylcellulose | 5 |
| Example 40: | Griseofulvin | 75% (W/W) |
| | Lactose | 10 |
| | Povidone (PVP) | 10 |
| | Polyethylene glycol 2000 | 5 |
| Example 41: | Terbinafine HCl | 75% (W/W) |
| | Polyethylene glycol 4000 | 10 |
| | Povidone (PVP) | 10 |
| | Hydroxypropylcellulose | 5 |
| Example 42: | Terbinafine HCl | 75% (W/W) |
| | Lactose | 15 |
| | Polyethylene glycol 4000 | 5 |
| | Polyvinylpyrrolidone | 5 |
| Example 43: | Ketoconazole | 40% (W/W) |
| | Eudragit S100 | 50 |
| | Triethyl Citrate | 10 |
| Example 44: | Ketoconazole | 50% (W/W) |
| | Sureteric | 50 |
| Example 45: | Ketoconazole | 50% (W/W) |
| | Eudragit S100 | 45 |
| | Triethyl Citrate | 5 |

Three Pulses

EXAMPLE 46

1. Antifungal Matrix Pellet Formulation and Preparation Procedure (Immediate Release)

A. Pellet Formulation

The composition of the antifungal matrix pellets provided in Table 1.

TABLE 1

Composition of Antifungal Pellets

| Component | Percentage (%) |
|---|---|
| Antifungal | 50 |
| Avicel PH 101 | 20 |
| Lactose | 20 |
| PVP K29/32* | 10 |
| Purified Water | |
| Total | 100 |

*PVP K29/32 was added as a 20% w/w aqueous solution during wet massing.

B. Preparation Procedure for antifungal Matrix Pellets 1.2.1 Blend metronidazole and Avicel® PH 101 using a Robot Coupe high shear granulator.
1.2.2 Add 20% Povidone K29/32 binder solution slowly into the powder blend under continuous mixing.
1.2.3 Extrude the wet mass using an LCI Bench Top Granulator. The diameter of the screen of the Bench Top Granulator was 1.0 mm.
1.2.4 Spheronize the extrudate using a Model SPH20 Caleva Spheronizer.
1.2.5 Dry the spheronized pellets at 50° C. overnight.
1.2.6 Pellets between 16 and 30 Mesh were collected for further processing.

The above procedure is used to make pellets of a first antifungal and pellets of a second different antifungal.

1.3 Preparation of an Eudragit® L 30 D-55 Aqueous Coating Dispersion

A. Dispersion Formulation

The composition of the aqueous Eudragit L30D-55 dispersion applied to the antifungal matrix pellets is provided below in Table 2.

TABLE 2

Eudragit ® L 30 D-55 Aqueous Coating Dispersion

| Component | Percentage (%) |
|---|---|
| Eudragit ® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

B. Preparation Procedure for an Eudragit® L 30 D-55 Aqueous Dispersion 1.3.1 Suspend triethyl citrate and talc in deionized water.
1.3.2 The TEC/talc suspension is then homogenized using a PowerGen 700 high shear mixer.
1.3.3 Add the TEC/talc suspension slowly to the Eudragit® L 30 D-55 latex dispersion while stirring.
1.3.4 Allow the coating dispersion to stir for one hour prior to application onto the antifungal matrix pellets.

1.4 Preparation of an Eudragit® S 100 Aqueous Coating Dispersion

A. Dispersion Formulation

The composition of the aqueous Eudragit® S 100 dispersion applied to the antifungal matrix pellets is provided below in Table 3.

TABLE 3

Eudragit ® S 100 Aqueous Coating Dispersion

| Component | Percentage (%) |
|---|---|
| Part A | |
| Eudragit ® S 100 | 12.0 |
| 1 N Ammonium Hydroxide | 6.1 |
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

B. Preparation Procedure for an Eudragit® S 100 Aqueous Dispersion

Part I:
  (i) Dispense Eudragit® S 100 powder in deionized water with stirring.
  (ii) Add ammonium hydroxide solution drop-wise into the dispersion with stirring.
  (iii) Allow the partially neutralized dispersion to stir for 60 minutes.
  (iv) Add triethyl citrate drop-wise into the dispersion with stirring. Stir for about 2 hours prior to the addition of Part B.

Part II:
  (i) Disperse talc in the required amount of water
  (ii) Homogenize the dispersion using a PowerGen 700D high shear mixer.
  (iii) Part B is then added slowly to the polymer dispersion in Part A with a mild stirring.

1.5 Coating Conditions for the Application of Aqueous Coating Dispersions

The following coating parameters are used to coat matrix pellets with each of the Eudragit® L 30 D-55 and Eudragit® S 100 aqueous film coating.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

(i) Coat matrix pellets with L30 D-55 dispersion such that you apply 12% coat weight gain to the pellets.
  (ii) Coat matrix pellets with S100 dispersion such that you apply 20% coat weight gain to the pellets.

1.6 Encapsulation of the Antifungal Pellets

Pellets are filled into size 00 hard gelatin capsules at a ratio of 30%: 30%: 40%: Immediate-release matrix pellets uncoated, L30 D-55 coated pellets and S100 coated pellets respectively. The capsule is filled with the three different pellets to achieve a the desire dosage.

The immediate release matrix pellets include the first antifungal, the L30 D-55 coated pellets are made by coating matrix pellets that contain the second antifungal and the S100 coated pellets are made by coating matrix pellets that contain the first antifungal.

Three Pulses

EXAMPLE 47

Antifungal Pellet Formulation and Preparation Procedure 47.1 Pellet Formulations for Subsequent Coating The composition of the Antifungaltrihydrate matrix pellets provided in Table 4.

TABLE 4

Composition of AntifungalMatrix Pellets

| Component | Percentage (%) |
|---|---|
| AntifungalTrihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

47.2 Preparation Procedure for AntifungalMatrix Pellets 47.2.1 Blend Antifungaland Avicel® PH 101 using a low shear blender.
47.2.2 Add the hydroxypropyl methylcellulose binder solution slowly into the powder blend under continuous mixing.
47.2.3 Extrude the wet mass using an LCI Bench Top Granulator. The diameter of the screen of the Bench Top Granulator is 0.8 mm.
47.2.4 Spheronize the extrudate using a QJ-230 Spheronizer using a small cross section plate.
47.2.5 Dry the spheronized pellets at 60° C. using a fluid bed dryer until the exhaust temperature reaches 40° C.
47.2.6 Pellets between 20 and 40 Mesh were collected for further processing.
47.2.7 The above procedure is used to produce pellets that contain a first antifungal and pellets that contain a second and different antifungal.

47.3 Preparation of an Eudragit® L 30 D-55 Aqueous Coating Dispersion

47.3.1 Dispersion Formulation

The composition of the aqueous Eudragit L30D-55 dispersion applied to the Antifungalmatrix pellets is provided below in Table 5.

TABLE 5

Eudragit® L 30 D-55 Aqueous Coating Dispersion

| Component | Percentage (%) |
|---|---|
| Eudragit® L 30 D-55 | 41.6 |
| Triethyl Citrate | 2.5 |
| Talc | 5.0 |
| Purified Water | 50.9 |
| Solids Content | 20.0 |
| Polymer Content | 12.5 |

47.4 Preparation Procedure for an Eudragit® L 30 D-55 Aqueous Dispersion 47.4.1 Suspend triethyl citrate and talc in deionized water.

47.4.2 The TEC/talc suspension is mixed using laboratory mixer.

47.4.3 Add the TEC/talc suspension from slowly to the Eudragit® L 30 D-55 latex dispersion while stirring.

47.4.4 Allow the coating dispersion to stir for one hour prior to application onto the Antifungalmatrix pellets.

47.5 Preparation of an Eudragit® S 100 Aqueous Coating Dispersion

47.5.1 Dispersion Formulation

The composition of the aqueous Eudragit® S 100 dispersion applied to the Antifungalmatrix pellets is provided below in Table 6.

TABLE 6

Eudragit® S 100 Aqueous Coating Dispersion

| Component | Percentage (%) |
|---|---|
| Part A | |
| Eudragit® S 100 | 10.0 |
| 1 N Ammonium Hydroxide | 5.1 |
| Triethyl Citrate | 5.0 |
| Water | 64.9 |
| Part B | |
| Talc | 5.0 |
| Water | 10.0 |
| Solid Content | 25.0 |
| Polymer Content | 10.0 |

47.6 Preparation Procedure for an Eudragit® S 100 Aqueous Dispersion

Part A:

47.6.1 Dispense Eudragit® S 100 powder in deionized water with stirring.

47.6.2 Add ammonium hydroxide solution drop-wise into the dispersion with stirring.

47.6.3 Allow the partially neutralized dispersion to stir for 60 minutes.

47.6.4 Add triethyl citrate drop-wise into the dispersion with stirring and let stir overnight prior to the addition of Part B.

Part B:

47.6.5 Disperse talc in the required amount of water 47.6.6 Stir the dispersion using an overhead laboratory mixer.

47.6.7 Part B is then added slowly to the polymer dispersion in Part A with a mild stirring.

47.7 Coating Conditions for the Application of Aqueous Coating Dispersions

The following coating parameters are used for both the Eudragit® L 30 D-55 and Eudragit® S 100 aqueous film coating processes.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2–6 gram per minute |

47.7.1 Coat matrix pellets with L30 D-55 dispersion such that you apply 20% coat weight gain to the pellets.

47.7.2 Coat matrix pellets with S100 dispersion such that you apply 37% coat weight gain to the pellets.

47.8 Preparation of AntifungalGranulation (Immediate Release Component) for tabletting

TABLE 7

Composition of AntifungalGranulation

| Component | Percentage (%) |
|---|---|
| AntifungalTrihydrate powder | 92 |
| Avicel PH 101 | 7.0 |
| Hydroxypropyl methylcellulose, NF* | 1.0 |
| Total | 100.0 |

*Hydroxypropyl methylcellulose was added as a 2.9% w/w aqueous solution during wet massing.

47.8.1 Blend Antiftungaland Avicel® PH 101 using a low shear blender.

47.8.2 Add the hydroxypropyl methylcellulose binder solution slowly into the powder blend under continuous mixing.

47.8.3 Dry the granulation at 60° C. using a fluid bed dryer until the exhaust temperature reaches 40° C.

47.8.4 Granules between 20 and 40 Mesh are collected for further processing.

47.9 Tabletting of the AntifungalPellets

TABLE 8

Composition of AntifungalTablets

| Component | Percentage (%) |
|---|---|
| First antifungalgranules | 32.5 |
| Avicel PH 200 | 5.0 |
| Second antifungalL30D-55 coated pellets | 30 |
| First antifungalS100 coated pellets | 30 |
| Colloidal silicon dioxide | 1.5 |
| Magnesium stearate | 1.0 |
| Total | 100 |

47.9.1 Blend the Antifungalgranules, Avicel PH-200, Antifungalpellets and colloidal silicon dioxide for 15 minutes in a tumble blender.

47.9.2 Add the magnesium stearate to the blender, and blend for 5 minutes.

47.9.3 Compress the blend on a rotary tablet press.

47.9.4 The fill weight should be adjusted to achieve the desired dosage.

Four Pulses

EXAMPLE 48

1 Antifungal Matrix Pellet Formulation and Preparation Procedure 48.1 Pellet Formulation The composition of the antifungal matrix pellets provided in Table 9.

TABLE 9

Composition of Antifungal Pellets

| Component | Percentage (%) |
|---|---|
| Antifungal | 50 |
| Avicel PH 101 | 20 |
| Lactose | 20 |
| PVP K29/32* | 10 |
| Purified Water |  |
| Total | 100 |

*PVP K29/32 was added as a 20% w/w aqueous solution during wet massing.

48.2 Preparation Procedure for Antifungal Matrix Pellets 48.2.1 Blend antifungal and Avicel® PH 101 using a Robot Coupe high shear granulator.

48.2.2 Add 20% Povidone K29/32 binder solution slowly into the powder blend under continuous mixing.

48.2.3 Extrude the wet mass using an LCI Bench Top Granulator. The diameter of the screen of the Bench Top Granulator was 1.0 mm.

48.2.4 Spheronize the extrudate using a Model SPH20 Caleva Spheronizer.

48.2.5 Dry the spheronized pellets at 50° C. overnight.

48.2.6 Pellets between 16 and 30 Mesh were collected for further processing.

48.2.7 The above procedure is used to prepare pellets that contain a first antifungal and pellets that contain a second antifungal.

48.3 Preparation of an Eudragit® L 30 D-55 Aqueous Coating Dispersion 48.3.1 Dispersion Formulation The composition of the aqueous Eudragit L30D-55 dispersion applied to the antifungal matrix pellets is provided below in Table 10.

TABLE 10

Eudragit ® L 30 D-55 Aqueous Coating Dispersion

| Component | Percentage (%) |
|---|---|
| Eudragit ® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

48.4 Preparation Procedure for an Eudragit® L 30 D-55 Aqueous Dispersion 48.4.1 Suspend triethyl citrate and talc in deionized water.

48.4.2 The TEC/talc suspension is then homogenized using a PowerGen 700 high shear mixer.

48.4.3 Add the TEC/talc suspension slowly to the Eudragit® L 30 D-55 latex dispersion while stirring.

48.4.4 Allow the coating dispersion to stir for one hour prior to application onto the antifungal matrix pellets.

48.5 Preparation of an Eudragit® S 100 Aqueous Coating Dispersion 48.5.1 Dispersion Formulation The composition of the aqueous Eudragit® S 100 dispersion applied to the antifungal matrix pellets is provided below in Table 11.

TABLE 11

Eudragit ® S 100 Aqueous Coating Dispersion

| Component | Percentage (%) |
|---|---|
| Part A |  |
| Eudragit ® S 100 | 12.0 |
| 1 N Ammonium Hydroxide | 6.1 |
| Triethyl Citrate | 6.0 |
| Purified Water | 65.9 |
| Part B |  |
| Talc | 2.0 |
| Purified Water | 8.0 |
| Solid Content | 20.0 |
| Polymer Content | 12.0 |

48.6 Preparation Procedure for an Eudragit® S 100 Aqueous Dispersion

Part A:

48.6.1 Dispense Eudragit® S 100 powder in deionized water with stirring.

48.6.2 Add ammonium hydroxide solution drop-wise into the dispersion with stirring.

48.6.3 Allow the partially neutralized dispersion to stir for 60 minutes.

48.6.4 Add triethyl citrate drop-wise into the dispersion with stirring. Stir for about 2 hours prior to the addition of Part B.

Part B:

48.6.5 Disperse talc in the required amount of water 48.6.6 Homogenize the dispersion using a PowerGen 700D high shear mixer.

48.6.7 Part B is then added slowly to the polymer dispersion in Part A with a mild stirring.

48.7 Coating Conditions for the Application of Aqueous Coating Dispersions

The following coating parameters are used for coating with each of the Eudragit® L 30 D-55 and Eudragit® S 100 aqueous film coatings.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

48.7.1 Coat matrix pellets with L30 D-55 dispersion such that you apply 12% coat weight gain to the pellets.

48.7.2 Coat matrix pellets with L30 D-55 dispersion such that you apply 30% coat weight gain to the pellets.

48.7.3 Coat matrix pellets with S100 dispersion such that you apply 20% coat weight gain to the pellets.

48.8 Encapsulation of the Antifungal Pellets

Pellets are filled into size 00 hard gelatin capsules at a ratio of 20%: 30%: 20%: 30% Immediate-release matrix pellets (uncoated), L30 D-55 coated pellets 12% weight gain, L30D-55 coated pellets 30% weight gain and S100 coated pellets respectively.

The capsule is filled with the four different pellets to achieve the desired dosage.

The immediate release pellets contain the first antifungal; the L30 D-55 12% weight gain coated pellets containe the second antifungal; the L30 D-55 30% weight gain coated pellets contain the first antifungal and the S100 coated pellets contain the second antifungal.

The present invention is advantageous in that a synergistic anti-fungal will be dosed in an alternate pulse to another, synergistic anti-fungal. This will alternate the exposure to the fungus in such a way as to make both anti-fungals more effective than if they were co-administered.

Numerous modifications and variations of the present invention are possible in light of the above teachings; therefore, within the scope of the appended claims, the invention may be practiced otherwise than as particularly described.

What is claimed is:

1. A once-a-day anti-fungal product comprising: first, second, and third dosage forms, wherein each of said dosage forms includes at least one anti-fungal agent and a pharmaceutically acceptable carrier; wherein at least one of said dosage forms includes at least a first anti-fungal agent and wherein at least one of said dosage forms includes at least a second anti-fungal agent, said second anti-fungal agent being different than said first anti-fungal agent; said first dosage form is an immediate release dosage form; said second and third dosage forms are delayed release dosage forms; each of said first, second, and third dosage forms initiates release of the anti-fungal agent(s) at different times; the Cmax in serum of the total anti-fungal agents released from said anti-fungal product is achieved in less than about 12 hours from administration; said once-a-day anti-fungal product contains the total dosage of said at least two different anti-fungal agents for a twenty-four hour period, and wherein at least one of said three dosage forms contains both the first and the second anti-fungal agents.

2. The product of claim 1, wherein anti-fungal released from the second dosage form reaches a Cmax in serum afier anti-fungal released from the first dosage reaches a Cmax in serum.

3. The product of claim 2, wherein anti-fungal released form the third dosage form reaches a Cmax in serum after anti-fungal released from the second dosage form reaches Cmax in serum.

4. The product of claim 1, wherein each of the three dosage forms includes at least the first and second anti-fungals.

5. The product of claim 1, wherein the first dosage form includes the first anti-fungal, the second dosage form includes the first and second anti-fungals, and the third dosage form includes the second anti-fungal.

6. The product of claim 1, wherein the immediate release dosage form contains from 20% to 50% of the total dosage of anti-fungal.

7. The product of claim 1, wherein said second dosage form initiates release of anti-fungal before said third dosage form, wherein said second dosage form provides from 30% to 60% by weight of the total anti-fungal released by said second and third dosage forms, and wherein said third dosage form provides the remainder of the total anti-fungal released by said second and third dosage forms.

8. The product of claim 1, wherein anti-fungal released from the second dosage form reaches a Cmax in serum in no more than about 4 hours after administration of the product.

9. The product of claim 1, wherein anti-fungal released from the third dosage form reaches a Cmax in serum within 8 hours after administration of the product.

10. The product of claim 1, wherein the product is an oral dosage form.

11. The product of claim 1 further comprising: a fourth dosage form, and wherein said first dosage form contains said first anti-fungal; said second dosage form contains said first anti-fungal; said third dosage form contains said second anti-fungal; said fourth dosage form includes said second anti-fungal and a pharmaceutically acceptable carrier; and said second and third dosage forms have release profiles whereby $C_{max}$ in serum for the first anti-fungal and $C_{max}$ in serum for the second anti-fungal released from the second and third dosage forms respectively are reached later in time than $C_{max}$ in serum is reached for the first anti-fungal released from the first dosage form, and whereby the $C_{max}$ in serum for the second anti-fungal released from the fourth dosage form is reached at a time after $C_{max}$ in serum for anti-fungal released from each of the first, second, and third dosage forms are reached.

12. The product of claim 11, wherein the first anti-fungal released from the second dosage form, and the second anti-fungal released from the third dosage form reach a $C_{max}$ in serum at about the same time.

13. The product of claim 11, wherein said fourth dosage form is a sustained release dosage form.

14. The product of claim 11, wherein said fourth dosage form is a delayed release dosage form.

15. The product of claim 14, wherein the immediate release dosage form contains from 15% to 30% of the total dosage of anti-fungal.

16. The product of claim 14, wherein said second dosage form initiates release of anti-fungal before said third dosage form; wherein said third dosage form initiates release of anti-fungal before said fourth dosage form; wherein said second dosage form provides 20% to 35% by weight of the total anti-fungal released by said second, third, and fourth dosage forms; wherein said third dosage form provides from 20% to 40% by weight of the total anti-fungal released by said second, third, and fourth dosage forms; and wherein said fourth dosage form provides the remainder of the total anti-fungal released by said second, third, and fourth dosage forms.

17. The product of claim 11, wherein anti-fungal released from the second dosage form reaches a Cmax in serum in no more than about 4 hours after administration of the product.

18. The product of claim 11, wherein anti-fungal released from the third dosage form reaches a Cmax in serum within 8 hours after administration of the product.

19. The product of claim 11, wherein the product is an oral dosage form.

20. A process for treating a fungus infection in a host comprising:
 administering to the host the anti-fungal product of claim 1 once-a-day.

21. A process for treating a fungus infection in a host comprising:
 administering to the host the anti-fungal product of claim 2 once-a-day.

22. A process for treating a fungus infection in a host comprising:
 administering to the host the anti-fungal product of claim 3 once-a-day.

23. A process for treating a fungus infection in a host comprising:
administering to the host the anti-fungal product of claim 4 once-a-day.

24. A process for treating a fungus infection in a host comprising:
administering to the host the anti-fungal product of claim 5 once-a-day.

25. A process for treating a fungus infection in a host comprising:
administering to the host the anti-fungal product of claim 6 once-a-day.

26. A process for treating a fungus infection in a host comprising:
administering to the host the anti-fungal product of claim 7 once-a-day.

27. A process for treating a fungus infection in a host comprising:
administering to the host the anti-fungal product of claim 8 once-a-day.

28. A process for treating a fungus infection in a host comprising:
administering to the host the anti-fungal product of claim 9 once-a-day.

29. A process for treating a fungus infection in a host comprising:
administering to the host the anti-fungal product of claim 10 once-a-day.

30. A process for treating a fungus infection in a host comprising:
administering to the host the anti-fungal product of claim 11 once-a-day.

31. A process for treating a fungus infection in a host comprising:
administering to the host the anti-fungal product of claim 12 once-a-day.

32. A process for treating a fungus infection in a host comprising:
administering to the host the anti-fungal product of claim 13 once-a-day.

33. A process for treating a fungus infection in a host comprising:
administering to the host the anti-fungal product of claim 14 once-a-day.

34. A process for treating a fungus infection in a host comprising:
administering to the host the anti-fungal product of claim 15 once-a-day.

35. A process for treating a fungus infection in a host comprising:
administering to the host the anti-fungal product of claim 16 once-a-day.

36. A process for treating a fungus infection in a host comprising:
administering to the host the anti-fungal product of claim 17 once-a-day.

37. A process for treating a fungus infection in a host comprising:
administering to the host the anti-fungal product of claim 18 once-a-day.

38. A process for treating a fungus infection in a host comprising:
administering to the host the anti-fungal product of claim 19 once-a-day.

39. A process for treating a patient with two different anti-fungal agents said process for treating comprising:
administering to a patient once-a-day an anti-fungal product, said product comprising: first, second, and third dosage forms, wherein each of said dosage forms includes at least one anti-fungal agent and a pharmaceutically acceptable carrier; wherein at least one of said dosage forms includes at least a first anti-fungal agent and wherein at least one of said dosage forms includes at least a second anti-fungal agent, said second anti-fungal agent being different than said first anti-fungal agent; wherein at least one of said three dosage forms contains both the first and the second anti-fungal agents said treating including an immediate release of anti-fungal agent from said first dosage form and delayed releases of anti-fungal agent from each of said second and third dosage forms, said immediate release and two delayed releases initiating release of anti-fungal agent at different times and achieving the Cmax in serum of the total anti-fungal agents released from said anti-fungal product in less than about 12 hours from administration; and said treating delivers the total dosage of said first and second anti-fungal agents for a twenty-four hour period.

* * * * *